(12) United States Patent
Morley et al.

(10) Patent No.: US 7,553,868 B2
(45) Date of Patent: Jun. 30, 2009

(54) THIOPHENE CARBOXAMIDES AS INHIBITORS OF THE ENZYME IKK-2

(75) Inventors: Andrew David Morley, Macclesfield (GB); Jeffrey Philip Poyser, Macclesfield (GB)

(73) Assignee: AstraZeneca AB (SE)

( * ) Notice: Subject to any disclaimer, the term of this patent is extended or adjusted under 35 U.S.C. 154(b) by 88 days.

(21) Appl. No.: 10/542,044

(22) PCT Filed: Jan. 13, 2004

(86) PCT No.: PCT/GB2004/000106

§ 371 (c)(1),
(2), (4) Date: Jul. 13, 2005

(87) PCT Pub. No.: WO2004/063185

PCT Pub. Date: Jul. 29, 2004

(65) Prior Publication Data

US 2006/0111431 A1    May 25, 2006

(30) Foreign Application Priority Data

Jan. 15, 2003    (SE) ..................... 0300091

(51) Int. Cl.
*A61K 31/38* (2006.01)
*C07D 333/32* (2006.01)
*C07D 333/34* (2006.01)
*C07D 333/36* (2006.01)
*C07D 333/42* (2006.01)

(52) U.S. Cl. .................. 514/445; 514/447; 514/448; 549/63; 549/64; 549/69; 549/72

(58) Field of Classification Search .................. 549/63, 549/64, 69, 72; 514/445, 447, 448
See application file for complete search history.

(56) References Cited

U.S. PATENT DOCUMENTS

| | | | |
|---|---|---|---|
| 3,963,750 A | 6/1976 | Goudie | |
| 5,258,357 A | 11/1993 | Muenster et al. | |
| 5,571,810 A | 11/1996 | Matsuo et al. | |
| 5,679,670 A | 10/1997 | Dean et al. | |
| 6,048,880 A | 4/2000 | Kawai et al. | |
| 6,380,214 B1 | 4/2002 | Gant et al. | |
| 6,414,013 B1 * | 7/2002 | Fancelli et al. | 514/438 |
| 6,699,854 B2 | 3/2004 | Wang et al. | |
| 6,809,088 B2 | 10/2004 | Chabrier de Lassauniere et al. | |
| 6,835,745 B2 * | 12/2004 | Coghlan et al. | 514/448 |
| 6,875,790 B2 * | 4/2005 | Bertenshaw et al. | 514/431 |
| 6,881,735 B2 * | 4/2005 | Schindler et al. | 514/227.8 |
| 6,881,741 B2 * | 4/2005 | Chan Chun Kong et al. | 514/91 |
| 7,019,027 B2 * | 3/2006 | Linden et al. | 514/447 |
| 7,084,170 B2 * | 8/2006 | Grossman et al. | 514/445 |
| 7,084,171 B2 * | 8/2006 | Grainger et al. | 514/445 |
| 7,098,240 B2 * | 8/2006 | Griffiths et al. | 514/447 |
| 7,125,896 B2 | 10/2006 | Faull et al. | |
| 7,166,369 B2 | 1/2007 | Wan et al. | |
| 7,196,106 B2 * | 3/2007 | Duffy et al. | 514/364 |
| 7,358,376 B2 | 4/2008 | Baxter et al. | |
| 2006/0058522 A1 | 3/2006 | Faull et al. | |
| 2006/0111431 A1 | 5/2006 | Morley et al. | |
| 2007/0015819 A1 | 1/2007 | Faull et al. | |

FOREIGN PATENT DOCUMENTS

| | | |
|---|---|---|
| EP | 0202538 | 11/1986 |
| EP | 0853083 | 7/1998 |
| EP | 0908456 | 4/1999 |
| GB | 1468012 | 3/1977 |
| GB | 2195634 | 4/1988 |
| WO | WO 98/02430 | 1/1998 |
| WO | WO 98/54116 | 12/1998 |
| WO | WO 99/46244 | 9/1999 |
| WO | WO 00/71532 | 11/2000 |
| WO | WO 01/58890 | 8/2001 |
| WO | WO 01/98290 | 12/2001 |
| WO | WO 02/30353 | 4/2002 |
| WO | WO 02/46171 A2 * | 6/2002 |
| WO | WO 03/010158 | 2/2003 |
| WO | WO 03/010163 | 2/2003 |
| WO | WO 03/028731 | 4/2003 |
| WO | WO 03/029241 | 4/2003 |
| WO | WO 2004/063185 | 7/2004 |
| WO | WO 2004/063186 | 7/2004 |

OTHER PUBLICATIONS

Parrish, Cynthia A. et al, CA138: 304 153 , 2003.*
M. Gripenberg, Scand. J. Rheumatology, vol. 10, No. 2, 1981, pp. 85-91.*
Cancer and Metastasis Reviews (1998), 17(1), 91-106.*
Science (1999), vol. 286, 531-537.*
Awada et al., "The pipeline of new anticancer agents for breast cancer treatment in 2003", *Clinical Reviews in Oncology/Hematology* 48:45-63 (2003).

(Continued)

*Primary Examiner*—Rebecca L Anderson
(74) *Attorney, Agent, or Firm*—Fish & Richardson P.C.

(57) ABSTRACT

The invention relates to thiophene carboxamides of formula (I) wherein Ar, R1, R2, R3, R4, R5, m and n are as defined in the specification, processes and intermediates used in their preparation, pharmaceutical compositions containing them and their use in therapy.

12 Claims, No Drawings

OTHER PUBLICATIONS

Berkow et al., The Merck Manual of Diagnosis and Therapy, 16$^{th}$ Edition, © 1992, Merck Research Laboratories, Rahway, NJ, pp. 1488-2664.

Chen et al., "TNF-R1 Signaling: A Beautiful Pathway", *Science* 296: 1634-1635 (2002).

Compston et al., "Multiple sclerosis", *The Lancet* 359:1221-1231 (2002).

Du et al., "Aryl ureas represent a new class of anti-trypanosomal agents", *Chemistry & Biology* 7:733-742 (2000).

Hartung et al., "What do we know about the mechanism of action of disease-modifying treatments in MS?" *J Neurol* 251(Suppl. 5):V/12-v/29 (2004).

Karin et al., "NF-$_k$B in cancer: from innocent bystander to major culprit", *Nat. Rev. Cancer* 2:301-310 (2002).

Luo et al., "IKK/NF-$_k$B signaling: balancing life and death - a new approach to cancer therapy", *J. Clin. Invest.* 115(10):2625-2632 (2005).

Orlowski, et al., "NF-$_k$B as a therapeutic target in cancer", *Trends in Molecular Medicine* 8(8):385-389 (2002).

Zayed et al., "Studies on 5-aminopyrazole derivatives, Synthesis of some new fused pyrazole derivatives", *Monash. Chem.* 115:431-436 (1984).

Cancer [online], [retrieved on Jul. 6, 2007] Retrieved from the Internet, URL; http://www.nlm.nih.gov/medlineplus/cancer.html.

Cancer[online], [retrieved on Jul. 6, 2007] Retrieved from the Internet, URL; http://en.wikipedia.org/wiki/Cancer.

Diabetes Guide [online] [retrieved from the internet of Jun. 17, 2008] [URL; http://diabetes.webmd.com/guide/diabetes-overview].

\* cited by examiner

THIOPHENE CARBOXAMIDES AS INHIBITORS OF THE ENZYME IKK-2

CROSS-REFERENCE TO RELATED APPLICATIONS

This application is the National Stage of International Application No. PCT/GB2004/000106, filed Jan.13, 2004, which claims the benefit of Swedish Patent Application Serial No. 0300091-6, filed Jan.15, 2003. The contents of both prior applications are hereby incorporated by reference in their entireties.

FIELD OF THE INVENTION

The present invention relates to thiophene carboxamide derivatives, processes and intermediates used in their preparation, pharmaceutical compositions containing them and their use in therapy.

BACKGROUND OF THE INVENTION

The NF-κB (nuclear factor κB) family is composed of homo- and heterodimers of the Rel family of transcription factors. A key role of these transcription factors is to induce and co-ordinate the expression of a broad spectrum of pro-inflammatory genes including cytokines, chemokines, interferons, MHC proteins, growth factors and cell adhesion molecules (for reviews see Verma et. al., Genes Dev. 9:2723-35, 1995; Siebenlist et. al., Ann. Rev. Cell. Biol. 10:405-455, 1994; Bauerle and Henkel, Ann. Rev. Immunol., 12:141-179, 1994; Barnes and Karin, New Engl. J. Med., 336:1066-1071, 1997).

The most commonly found Rel family dimer complex is composed of p50 NFkB and p65 RelA (Baeuerle and Baltimore, Cell 53:211-217, 1988; Baeuerle and Baltimore, Genes Dev. 3:1689-1698, 1989). Under resting conditions NF-κB dimers are retained in the cytoplasm by a member of the IκB family of inhibitory proteins (Beg et. al., Genes Dev., 7:2064-2070, 1993; Gilmore and Morin, Trends Genet. 9:427-433, 1993; Haskil et. al., Cell 65:1281-1289, 1991). However, upon cell activation by a variety of cytokines or other external stimuli, IκB proteins become phosphorylated on two critical serine residues (Traenckner et. al., EMBO J., 14:2876, 1995) and are then targeted for ubiquitination and proteosome-mediated degradation (Chen, Z. J. et. al., Genes and Dev. 9:1586-1597, 1995; Scherer, D. C. et. al., Proc. Natl. Acad. Sci. USA 92:11259-11263, 1996; Alkalay, I. et. al., Proc. Natl. Acad. Sci. USA 92:10599-10603, 1995). The released NF-κB is then able to translocate to the nucleus and activate gene transcription (Beg et. al., Genes Dev., 6:1899-1913, 1992).

A wide range of external stimuli have been shown to be capable of activating NF-κB (Baeuerle, P. A., and Baichwal, V. R., Adv. Immunol., 65:111-136, 1997). Although the majority of NF-κB activators result in IκB phosphorylation, it is clear that multiple pathways lead to this key event. Receptor-mediated NF-κB activation relies upon specific interactions between the receptor and adapter/signalling molecules (for example, TRADD, RIP, TRAF, MyD88) and associated kinases (IRAK, NIK) (Song et. al., Proc. Natl. Acad. Sci. USA 94:9792-9796, 1997; Natoli et. al., JBC 272:26079-26082, 1997). Environmental stresses such as UV light and γ-radiation appear to stimulate NF-κB via alternative, less defined, mechanisms.

Recent publications have partially elucidated the NF-κB activation. This work has identified three key enzymes which regulate specific IκB/NF-κB interactions: NF-κB inducing kinase (NIK) (Boldin et. al., Cell 85:803-815, 1996), IκB kinase-1 (IKK-1) (Didonato et. al., Nature 388:548, 1997; Regnier at. al., Cell 90:373 1997) and IκB kinase-2 (IKK-2) (Woronicz et. al., Science 278:866, 1997; Zandi et. al., Cell 91:243, 1997).

NIK appears to represent a common mediator of NF-κB signalling cascades triggered by tumour necrosis factor and interleukin-1, and is a potent inducer of IκB phosphorylation. However NIK is unable to phosphorylate IκB directly.

IKK-1 and IKK-2 are thought to lie immediately downstream of NIK and are capable of directly phosphorylating all three IκB sub-types. IKK-1 and IKK-2 are 52% identical at the amino acid level but appear to have similar substrate specificities; however, enzyme activities appear to be different: IKK-2 is several-fold more potent than IKK-1. Expression data, coupled with mutagenesis studies, suggest that IKK-1 and IKK-2 are capable of forming homo- and heterodimers through their C-terminal leucine zipper motifs, with the heterodimeric form being preferred (Mercurio et. al., Mol. Cell Biol., 19:1526, 1999; Zandi et. al., Science; 281: 1360, 1998; Lee et. al, Proc. Natl. Acad. Sci. USA 95:9319, 1998).

NIK, IKK-1 and IKK-2 are all serine/threonine kinases. Recent data has shown that tyrosine kinases also play a role in regulating the activation of NF-κB. A number of groups have shown that TNF-α induced NF-κB activation can be regulated by protein tyrosine phosphatases (PTPs) and tyrosine kinases (Amer et. al., JBC 273:29417-29423, 1998; Hu et. al., JBC 273:33561-33565, 1998; Kaekawa et. al., Biochem. J. 337:179-184, 1999; Singh et. al., JBC 271 31049-31054, 1996). The mechanism of action of these enzymes appears to be in regulating the phosphorylation status of IκB. For example, PTP1B and an unidentified tyrosine kinase appear to directly control the phosphorylation of a lysine residue (K42) on IκB-α, which in turn has a critical influence on the accessibility of the adjacent serine residues as targets for phosphorylation by IKK.

Several groups have shown that IKK-1 and IKK-2 form part of a 'signalosome' structure in association with additional proteins including IKAP (Cohen et. al., Nature 395: 292-296, 1998; Rothwarf et. al., Nature 395:297-300, 1998), MEKK-1, putative MAP kinase phosphatase (Lee et. al., Proc. Natl. Acad. Sci. USA 95:9319-9324, 1998), as well as NIK and IκB. Data is now emerging to suggest that although both IKK-1 and IKK-2 associate with NIK, they are differentially activated, and therefore might represent an important integration point for the spectrum of signals that activate NF-κB. Importantly, MEKK-1 (one of the components of the putative signalosome and a target for UV light, LPS induced signalling molecules and small GTPases) has been found to activate IKK-2 but not IKK-1. Similarly, NIK phosphorylation of IKK-1 results in a dramatic increase in IKK-1 activity but only a small effect on IKK-2 (for review, see Mercurio, F., and Manning, A. M., Current Opinion in Cell Biology, 11:226-232, 1999).

Inhibition of NF-κB activation is likely to be of broad utility in the treatment of inflammatory disease.

There is accumulating evidence that NF-κB signalling plays a significant role in the development of cancer and metastasis. Abnormal expression of c-Rel, NF-κB2 or IκBα have been described in a number of tumour types and tumour cell lines, and there is now data to show that constitutive NF-κB signalling via IKK-2 takes place in a wide range of tumour cell lines. This activity has been linked to various upstream defects in growth factor signalling such as the establishment of autocrine loops, or the presence of oncogene products e.g. Ras, AKT, Her2, which are involved in the activation of the IKK complex. Constitutive NF-κB activity is believed to contribute to oncogenesis through activation of a range of anti-apoptotic genes e.g. A1/Bfi-1, IEX-1, XIAP, leading to the suppression of cell death pathways, and transcriptional upregulation of cyclin D1 which promotes cell growth. Other data indicate that this pathway is also likely to be involved in the regulation of cell adhesion and cell surface proteases. This suggests a possible additional role for NF-κB activity in the development of metastasis. Evidence confirming the involvement of NF-κB activity in oncogenesis includes the inhibition of tumour cell growth in vitro and in vivo on expression of a modified form of IκBα (super-repressor IκBα).

In addition to the constitutive NF-κB signalling observed in many tumour types, it has been reported that NF-κB is also activated in response to certain types of chemotherapy. Inhibition of NF-κB activation through expression of the super-repressor form of IκBα in parallel with chemotherapy treatment has been shown to enhance the anti-tumour effect of the chemotherapy in xenograft models. NF-κB activity is therefore also implicated in inducible chemoresistance.

Patent application WO 01/58890 discloses certain thiophene carboxamide derivatives that are useful as IKK-2 inhibitors. We now disclose a further group of thiophene carboxamide derivatives that possess desirable pharmacological activity profiles with beneficial pharmacokinetic properties.

DISCLOSURE OF THE INVENTION

According to the present invention, there is provided a compound of formula (I)

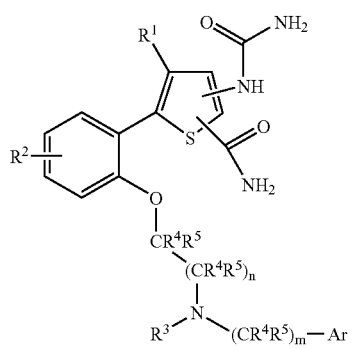

(I)

in which:

$R^1$ represents H or $CH_3$;

$R^2$ represents H, halogen, cyano, C1 to 2 alkyl, trifluoromethyl or C1 to 2 alkoxy;

n represents an integer 1, 2 or 3;

m represents an integer 0, 1, 2 or 3;

$R^3$ represents H, C2 to 4 alkenyl or C1 to 4 alkyl; said alkyl group being optionally further substituted by CN, C1 to 4 alkoxy, C1 to 4 alkyl—$SO_2$— or one or more fluoro atoms;

or $R^3$ represents a C1 to 4 alkylene group that forms a 4 to 7 membered azacyclic ring by virtue of being additionally bonded to either the aromatic ring, Ar, or to the linker group, —$CR^4R^5$—$(CR^4R^5)$—;

$R^4$ and $R^5$ independently represent H or C1 to 2 alkyl; or the group $CR^4R^5$ together represents a 3 to 6 membered carbocyclic ring that optionally incorporates one heteroatom selected from O or S; and each $R^4$, each $R^5$ and each group $CR^4R^5$ is selected independently;

Ar represents a phenyl ring or a 5- or 6-membered heteroaromatic ring containing one to three heteroatoms selected independently from O, N and S; said phenyl or heteroaromatic ring being optionally substituted by one or more substituents selected independently from halogen, cyano, C1 to 2 alkyl, trifluoromethyl, C1 to 2 alkoxy, $NR^6R^7$, —$CONR^6R^7$, —$COOR^6$, —$NR^6COR^7$, —$S(O)_pR^6$, —$SO_2NR^6R^7$ and —$NR^6SO_2R^7$;

$R^6$ and $R^7$ independently represent H, C2 to 4 alkenyl or C1 to 4 alkyl; said alkyl or alkenyl groups being optionally further substituted by one or more halogen atoms;

p represents an integer 0, 1 or 2;

and pharmaceutically acceptable salts thereof.

Certain compounds of formula (I) are capable of existing in stereoisomeric forms. It will be understood that the invention encompasses all geometric and optical isomers of the compounds of formula (I) and mixtures thereof, including racemates. Tautomers and mixtures thereof also form an aspect of the present invention.

In one embodiment, n in formula (I) represents the integer 1.

In another embodiment, $R^1$ in formula (I) represents H.

In another embodiment, $R^2$ in formula (I) represents H.

In another embodiment, m in formula (I) represents the integer 1.

In another embodiment, each $R^4$ and each $R^5$ in formula (I) represents H.

In yet another embodiment —$CR^4R^5$—$(CR^4R^5)n$- is linked to $R^3$ to form a 5 membered azacyclic ring together with $R^3$ and the nitrogen atom to which $R^3$ is attached.

In another embodiment, $R^3$ is hydrogen or C1 to 4 alkyl or $R^3$ represents a C1-4 alkylene group that forms a 4 to 7 membered azacyclic ring by virtue of being additionally bonded to either aromatic ring, Ar, or to the linker group, —$CR^4R^5$—$(CR^4R^5)n$-.

In yet another embodiment, $R^3$ is hydrogen or methyl or $R^3$ represents a C1 to 2 alkylene group that forms a 5 membered azacyclic ring by virtue of being additionally bonded to either aromatic ring, Ar, or to the linker group, —$CR^4R^5$—$(CR^4R^5)n$-.

In yet another embodiment, $R^3$ is hydrogen or methyl or $R^3$ represents a methylene group that forms a pyrrolidine ring with the nitrogen to which it is attached, —$(CR^4R^5)m$- and Ar by virtue of being additionally bonded to aromatic ring, Ar, when —$(CR^4R^5)m$- is methylene or $R^3$ represents an ethylene group that forms a pyrrolidine ring by virtue of being additionally bonded to the —$CR^4R^5$— group in —$CR^4R^5$—$(CR^4R^5)n$-, wherein n is 1.

In one embodiment $R^6$ and $R^7$ independently represent hydrogen or C1 to 4 alkyl.

In another embodiment $R^6$ and $R^7$ independently represent hydrogen or methyl or ethyl.

In one embodiment Ar is unsubstiuted or substituted by halogeno.

In one embodiment Ar is optionally substituted by 1, 2 or 3 substituents.

In another embodiment Ar is optionally substituted by 1 or 2 substituents.

In yet another embodiment Ar is optionally substituted by 1 substituent.

In another embodiment Ar is unsubstiuted.

In another embodiment, Ar in formula (I) represents optionally substituted phenyl.

In another embodiment, Ar in formula (I) represents optionally substituted pyridyl.

In one embodiment, the carboxamido group in formula (I) is attached to the 3-position of the thiophene ring.

In another embodiment, the carboxamido group in formula (I) is attached to the 2-position of the thiophene ring.

In one embodiment the present invention relates to compounds of formula (I) wherein n and m each represent the integer 1; $R^1$ and $R^2$ each represent H; each $R^4$ and each $R^5$ represents H; Ar represents optionally substituted phenyl or pyridyl; and $R^3$, $R^6$, $R^7$ and p are as defined above.

In one embodiment the present invention relates to compounds of formula (I) wherein n and m each represent the integer 1; $R^1$ and $R^2$ each represent H; each $R^4$ and each $R^5$ represents H; Ar represents optionally substituted phenyl or pyridyl; $R^3$ is hydrogen or methyl or $R^3$ represents a C1 to 2 alkylene group that forms a 5 membered azacyclic ring by virtue of being additionally bonded to either aromatic ring, Ar, or to the linker group, —$CR^4R^5$—$(CR^4R^5)$n-; $R^6$ and $R^7$ independently represent hydrogen or C1 to 4 alkyl and p is as defined above.

In one embodiment the present invention relates to compounds of formula (I) wherein n and m each represent the integer 1; $R^1$ and $R^2$ each represent H; each $R^4$ and each $R^5$ represents H; Ar represents optionally substituted phenyl or pyridyl; $R^3$ is hydrogen or methyl or $R^3$ represents a C1 to 2 alkylene group that forms a 5 membered azacyclic ring by virtue of being additionally bonded to either aromatic ring, Ar, or to the linker group, —$CR^4R^5$—$(CR^4R^5)$n-; and there are 1 or 2 optional substituents on Ar when it is phenyl and they are independently selected from halogeno and when Ar is a pyridyl group it is unsubstituted.

In one embodiment the present invention relates to compounds of formula (I) wherein n and m each represent the integer 1; $R^1$ and $R^2$ each represent H; each $R^4$ and each $R^5$ represents H; Ar represents optionally substituted phenyl or pyridyl; $R^3$ is hydrogen or methyl or $R^3$ represents a C1 to 2 alkylene group that forms a 5 membered azacyclic ring by virtue of being additionally bonded to either aromatic ring, Ar, or to the linker group, —$CR^4R^5$—$(CR^4R^5)$n-; and $R^6$, $R^7$ and p are as defined above.

The compounds of formula (I) and their pharmaceutically acceptable salts have the advantage that they are inhibitors of the enzyme IKK-2.

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof, for use as a medicament.

Another aspect of the invention provides the use of a compound of formula (I) or a pharmaceutically acceptable salt thereof, in the manufacture of a medicament, for the treatment or prophylaxis of diseases or conditions in which inhibition of IKK-2 activity is beneficial.

A more particular aspect of the invention provides the use of a compound of formula (I) or a pharmaceutically acceptable salt thereof, in the manufacture of a medicament, for the treatment or prophylaxis of inflammatory disease.

According to the invention, there is also provided a method of treating, or reducing the risk of, diseases or conditions in which inhibition of IKK-2 activity is beneficial which comprises administering to a person suffering from or at risk of, said disease or condition, a therapeutically effective amount of a compound of formula (I), or a pharmaceutically acceptable salt thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt thereof.

Particular compounds of the invention include those exemplified herein:

2-[(aminocarbonyl)amino]-5-[2-{2-[{N-(2-chlorobenzyl)-N-methyl}amino]ethoxy}phenyl]thiophene-3-carboxamide;

2-[(aminocarbonyl)amino]-5-[2-{2-[{N-(4-chlorobenzyl)-N-methyl}amino]ethoxy}phenyl]thiophene-3-carboxamide;

2-[(aminocarbonyl)amino]-5-[2-{2-(benzylamino)ethoxy}phenyl]thiophene-3-carboxamide;

2-[(aminocarbonyl)amino]-5-[2-{2-[N-benzyl-N-methylamino]ethoxy}phenyl]thiophene-3-carboxamide;

2-[(aminocarbonyl)amino]-5-[2-{2-(1,3-dihydro-2H-isoindol-2-yl)ethoxy}phenyl]thiophene-3-carboxamide;

2-[(aminocarbonyl)amino]-5-[2-{[1-(4-fluorobenzyl)pyrrolidin-3-yl]oxy}phenyl]thiophene-3-carboxamide;

2-[(aminocarbonyl)amino]-5-[2-{[1-benzylpyrrolidin-3-yl]oxy}phenyl]thiophene-3-carboxamide;

2-[(aminocarbonyl)amino]-5-[2-{2-[(4-fluorobenzyl)amino]ethoxy}phenyl]thiophene-3-carboxamide;

2-[(aminocarbonyl)amino]-5-[2-{2-(pyridin-3-ylmethylamino)ethoxy}phenyl]thiophene-3-carboxamide;

2-[(aminocarbonyl)amino]-5-[2-{2-(pyridin-2-ylmethylamino)ethoxy}phenyl]thiophene-3-carboxamide;

2-[(aminocarbonyl)amino]-5-[2-{2-(pyridin-4-ylmethylamino)ethoxy}phenyl]thiophene-3-carboxamide;

2-[(aminocarbonyl)amino]-5-[2-{2-[N-(pyridin-3-ylmethyl)-N-methylarmino]ethoxy}phenyl]thiophene-3-carboxamide;

3-[(aminocarbonyl)amino]-5-[2-{2-(1,3-dihydro-2H-isoindol-2-yl)ethoxy}phenyl]thiophene-2-carboxamide;

and pharmaceutically acceptable salts thereof.

Unless otherwise indicated, the term "C1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl. The term "C1 to 2 alkyl" is to be interpreted analogously.

Unless otherwise indicated, the term "C2 to 4 alkenyl" referred to herein denotes a straight or branched chain alkyl group having 2 to 4 carbon atoms incorporating at least one carbon-carbon double bond. Examples of such groups include ethenyl and propenyl.

Unless otherwise indicated, the term "C1 to 4 alkylene" referred to herein denotes a straight or branched chain alkyl group having 1 to 4 carbon atoms and offering two free valencies. Examples of such groups include methylene and ethylene.

Unless otherwise indicated, the term "C1 to 4 alkoxy" referred to herein denotes a straight or branched chain alkoxy group having 1 to 4 carbon atoms. Examples of such groups include methoxy, ethoxy and isopropoxy. The term "C1 to 2 alkoxy" is to be interpreted analogously.

Unless otherwise indicated, the term "halogen" referred to herein denotes fluoro, chloro, bromo and iodo.

Examples of a 4 to 7 membered azacyclic ring include pyrrolidine and piperidine.

Examples of a 5- or 6-membered heteroaromatic ring containing one to three heteroatoms independently selected from O, N and S include pyridyl, pyrimidine, furan, thiophene, isoxazole, triazole and pyrazole.

Examples of a 3 to 6 membered carbocyclic ring that optionally incorporates one heteroatom selected from O and S include cyclopropyl, cyclopentyl, cyclohexyl, tetrahydrofuranyl, tetrahydropyranyl, tetrahydrothienyl, pyrrolidinyl and piperidinyl.

According to the invention there is also provided a process for the preparation of a compound of formula (I) or a pharmaceutically acceptable salt, enantiomer or racemate thereof which comprises:

(a) reaction of a compound of formula (II):

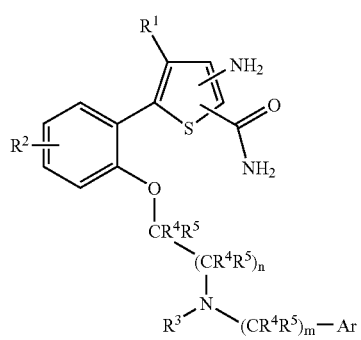

(II)

wherein $R^1$, $R^2$, $R^3$, $R^4$, $R^5$, Ar, m and n are as defined in formula (I), with an isocyanate; or (b) reaction of compound of formula (III)

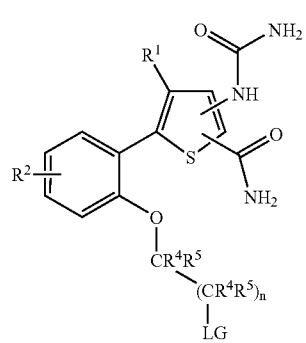

(III)

wherein $R^1$, $R^2$, $R^4$, $R^5$ and n are as defined in formula (I) and LG represents a leaving group, with an amine ($R^3$NH($CR^4R^5$)$_m$—Ar) wherein $R^3$, $R^4$, $R^5$, Ar and m are as defined in formula (I); or (c) reaction of compound of formula (IV)

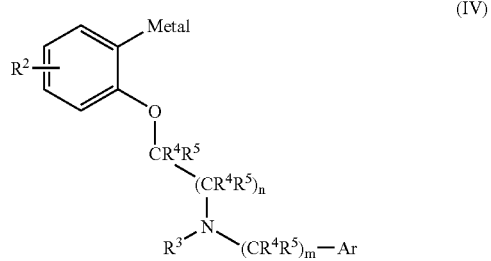

(IV)

wherein $R^2$, $R^3$, $R^4$, $R^5$, m, n and Ar are as defined in formula (I), with a compound of formula (V)

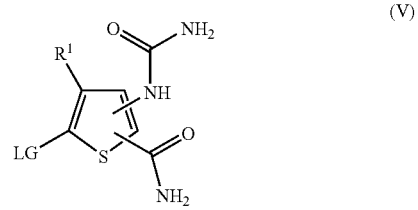

(V)

wherein $R^1$ is as defined in formula (I) and LG represents a leaving group; or (d) reaction of compound of formula (VI)

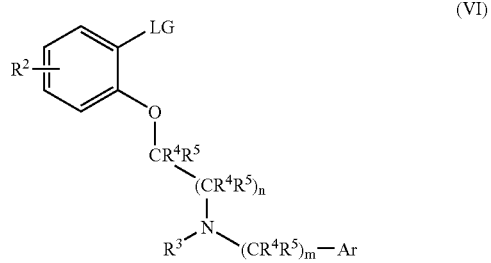

(VI)

wherein $R^2$, $R^3$, $R^4$, $R^5$, m, n and Ar are as defined in formula (I) and LG represents a leaving group, with a compound of formula (VII)

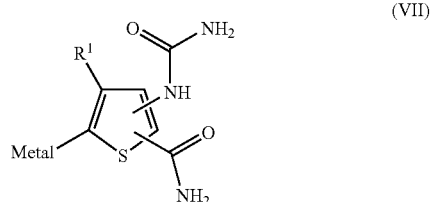

(VII)

wherein $R^1$ is as defined in formula (I);

and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

In process (a), suitable isocyanate reagents include trimethylsilylisocyanate, trichloroacetylisocyanate and sodium isocyanate. The reaction with trimethylsilylisocyanate can be carried out in a solvent such as dichloromethane/dimethylformamide at a suitable elevated temperature, for example, at the reflux temperature of the reaction mixture. The reaction with sodium isocyanate can be carried out in a suitable solvent system such as aqueous acetic acid at ambient temperature. The trichloroacetylisocyanate reaction can be carried out in a suitable solvent system such as acetonitrile at ambient temperature, and subsequently treating the mixture with ammonia to give compounds of the general formula (I). In a preferred embodiment, the isocyanate is trichloroacetylisocyanate.

In process (b), the compounds of formula (III) are reacted together with amines under appropriate reaction conditions. This can either be in the presence or absence of base. Such bases can be either inorganic or organic. Suitable leaving groups include iodo, bromo, chloro, sulphonate and triflate.

In processes (c) and (d), the compounds of formulae (IV) and (V) or of formulae (VI) and (VII) are reacted together under catalysis provided by a complex of a transition metal such as palladium or nickel. In compounds of formulae (IV) and (VII), under appropriate conditions, "metal" can be a metal or semi-metal such as magnesium, zinc, copper, tin, silicon, zirconium, aluminium or boron. Suitable leaving groups include iodo, bromo, chloro, triflate or phosphonate.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the addition and removal of one or more protecting groups.

The protection and deprotection of functional groups is described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley—Interscience (1999). The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (II) can be prepared by standard chemistry described in the literature [for example, J. Heterocyclic Chem., 36, 333 (1999)], or by reaction of compounds of formula (VI):

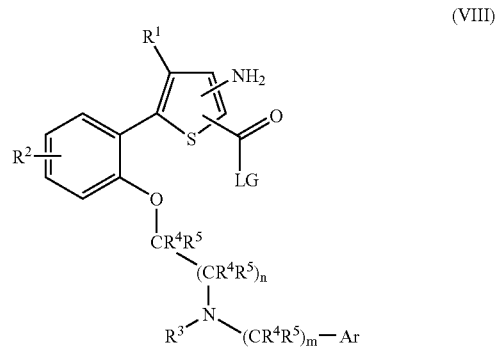

(VIII)

wherein $R^1$, $R^2$, $R^3$, $R^4$, $R^5$, Ar, m and n are as defined in formula (I), and LG represents a leaving group, with ammonia. Suitable groups LG include halogen, in particular, chloro.

Compounds of formula (VIII) where LG is halo can be prepared from the corresponding compound of formula (IX):

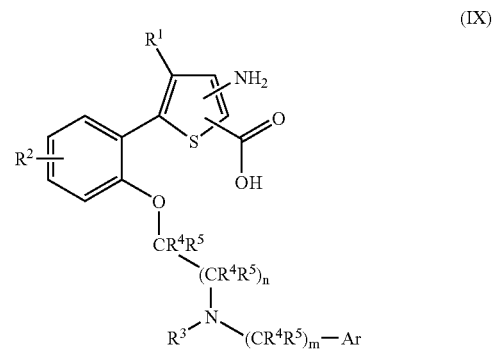

(IX)

wherein $R^1$, $R^2$, $R^3$, $R^4$, $R^5$, Ar, m and n are as defined in formula (I), by treatment with a halogenating agent such as thionyl chloride.

Compounds of formulae (III), (IV), (V), (VI), (VII) and (IX) are either commercially available or can be prepared using standard chemistry as exemplified herein.

Certain novel intermediate compounds form a further aspect of the invention.

The compounds of formula (I) have activity as pharmaceuticals, in particular as IKK-2 enzyme inhibitors, and may be used in the treatment (therapeutic or prophylactic) of conditions/diseases in human and non-human animals in which inhibition of IKK-2 is beneficial. Examples of such conditions/diseases include inflammatory diseases or diseases with an inflammatory component. Particular diseases include inflammatory arthritides including rheumatoid arthritis, osteoarthritis, spondylitis, Reiters syndrome, psoriatic arthritis, lupus and bone resorptive disease; multiple sclerosis, inflammatory bowel disease including Crohn's disease; asthma, chronic obstructive pulmonary disease, emphysema, rhinitis, myasthenia gravis, Graves' disease, allograft rejection, psoriasis, dermatitis, allergic disorders, immune complex diseases, cachexia, ARDS, toxic shock, heart failure, myocardial infarcts, atherosclerosis, reperfusion injury, AIDS, cancer and disorders characterised by insulin resistance such as diabetes, hyperglycemia, hyperinsulinemia, dyslipidemia, obesity, polycystic ovarian disease, hypertension, cardiovascular disease and Syndrome X.

The reported roles of NF-κB in both oncogenesis and chemoresistance suggest that inhibition of this pathway through the use of an IKK-2 inhibitor, such as a small molecule IKK-2 inhibitor, could provide a novel monotherapy for cancer and/or an important adjuvant therapy for the treatment of chemoresistant tumours and in the synergistic induction of apoptosis as a result of combination therapy with an IKK-2 inhibitor with standard therapies or other novel agents.

We are particularly interested in diseases selected from asthma, rheumatoid arthritis, psoriasis, inflammatory bowel disease including Crohn's disease, multiple sclerosis, chronic obstructive pulmonary disease, bone resorptive disease, osteoarthritis, diabetes/glycaemic control and cancer.

Thus, the present invention provides a compound of formula (I), or a pharmaceutically acceptable salt thereof, as hereinbefore defined for use in therapy.

In a further aspect, the present invention provides the use of a compound of formula (I), or a pharmaceutically acceptable salt thereof, as hereinbefore defined in the manufacture of a medicament for use in therapy.

In a still further aspect, the present invention provides the use of a compound of formula (I), or a pharmaceutically acceptable salt thereof, as hereinbefore defined in the manufacture of a medicament for the treatment of diseases or conditions in which modulation of the IKK-2 enzyme activity is beneficial.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating an IKK-2 mediated disease, which comprises administering to a patient a therapeutically effective amount of a compound of formula (I), or a pharmaceutically acceptable salt thereof, as hereinbefore defined.

The invention also provides a method of treating an inflammatory disease, especially asthma, rheumatoid arthritis or multiple sclerosis, in a patient suffering from, or at risk of, said disease, which comprises administering to the patient a therapeutically effective amount of a compound of formula (I), or a pharmaceutically acceptable salt thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt thereof, as hereinbefore defined, in association with a pharmaceutically acceptable adjuvant, diluent or carrier.

The invention further provides a process for the preparation of a pharmaceutical composition of the invention, which comprises mixing a compound of formula (I), or a pharmaceutically acceptable salt thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Conventional procedures for the selection and preparation of suitable pharmaceutical formulations are described in, for example, "Pharmaceuticals—The Science of Dosage Form Designs", M. E. Aulton, Churchill Livingstone, 1988.

In one aspect of the invention the composition may be adapted for administration by inhalation or insufflation. For example, the composition may be administered in a form suitable for inhalation, for example as a finely divided powder or a liquid aerosol such as an aerosol formed from a predominantly aqueous solution or suspension, or for administration by insufflation, for example as a finely divided powder.

It will be appreciated that delivery by inhalation or insufflation provides higher concentrations of the drug to the required site, namely the epithelial lining of the lung, than those readily achievable following systemic absorption of the drug. Smaller doses can therefore be used to delivered the drug locally to the specific cells which are to be controlled. Thereby, any adverse systemic side effects of the drug are reduced and the beneficial effects of the treatment can be realised more quickly.

Such administration may use a compressed gas to expel the drug from a container, for example an aerosol formulation may be used comprising fine liquid or solid particles carried by a propellant gas under pressure. The aerosol contains the drug which is dissolved, suspended or emulsified in a mixture of a fluid carrier and a propellant. Conventional propellants may be used, for example hydrocarbons or other suitable gases or mixtures thereof. Conventional metered dose aerosol and breath-activated delivery devices (MDIs) may be employed. Alternatively, the drug may be administered using a conventional nebuliser, which generates fine liquid particles of substantially uniform size containing the drug dispersed as small droplets that can penetrate into the respiratory tract of the patient. Alternatively, a powder composition containing the drug, with or without a lubricant, carrier or propellant, may be used. For example, a powder mixture of the compound and a suitable powder base such as lactose or starch may be presented in a unit dosage form that may be administered with the aid of an inhaler.

However, certain patients may produce copious quantities of mucus in the lungs and such patients may not be treatable initially by inhalation. In that event, it may be preferable to delivery the pharmaceutical composition of the present invention by injection or orally.

The compositions of the invention may be obtained by conventional procedures using conventional pharmaceutical excipients that are well known in the art. Thus, compositions intended for oral use may contain, for example, one or more colouring, sweetening, flavouring and/or preservative agents.

The invention is illustrated by the following examples:

The following abbreviations are used:

| | |
|---|---|
| DCM | Dichloromethane; |
| DMF | N,N-Dimethylformamide; |
| THF | Tetrahydrofuran. |

Unless otherwise indicated, organic solutions were dried using anhydrous magnesium sulphate. Unless otherwise indicated, cation exchange columns were eluted using ammonia/methanol mixtures.

EXAMPLE 1

2-[(Aminocarbonyl)amino]-5-[2-{2-[{N-(2-chlorobenzyl)-N-methyl}amino]ethoxy}phenyl]-thiophene-3-carboxamide a) N-[2-(2-Bromophenoxy)ethyl]-N-(2-chlorobenzyl)methylamine (1.75 g) was stirred in THF (15 ml) under argon. The solution was cooled to −78° C. and n-butyl lithium (3.4 ml, 1.6M solution in hexane) was added dropwise. The reaction mixture was stirred at −78° C. for 30 min, and tri-isopropylborate (1.88 g) added. The mixture was stirred for 1 h at room temperature and the solvents evaporated at reduced pressure. The residue was dissolved in dimethoxyethane (25 ml) and saturated aqueous sodium hydrogen carbonate (12 ml) added, followed by 2-[(aminocarbonyl)amino]-5-bromothiophene-3-carboxamide (0.35 g). Argon was bubbled through the stirred mixture at reflux for 5 min and Pd(PPh$_3$)$_4$ (0.1 g) added. The mixture was stirred for a flirter 2 h at reflux under argon, cooled and the dimethoxyethane evaporated under reduced pressure. The residue was stirred with water (10 ml) and DCM (30 ml) for 30 min and filtered. The solid was washed with water, DCM and methanol affording the title compound as a beige solid (0.204 g).

MS (ES) 459 (M+H)$^+$.

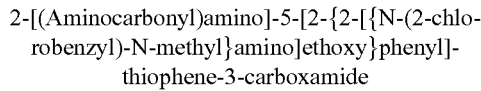

b) N-[2-(2-Bromophenoxy)ethyl]-N-(2-chlorobenzyl)methylamine

N-2-Chlorobenzylmethylamine (3.0 g), 1-bromo-2-(2-chloroethoxy)benzene (4.0 g) potassium iodide (0.165 g) and potassium carbonate (7.0 g) were heated in DMF (45 ml) with stirring at 115° C. for 18 h. The mixture was cooled, the solid filtered off and the DMF solution was evaporated, re-dissolved in ethyl acetate, adsorbed on to silica gel, evaporated and chromatographed in ethyl acetate-isohexane mixtures affording the product as an oil (1.7 g).

MS (ES) 354 (M+H)$^+$.

$^1$H NMR (CDCl$_3$) 2.4 (s, 3H), 3.0 (t, 2H), 3.75 (s, 2H), 4.2 (t, 2H), 6.7-6.9 (m, 2H), 7.15-7.3 (m, 3H), 7.3 (d, 1H), 7.5-7.6 (m, 2H).

EXAMPLE 2

2-[(Aminocarbonyl)amino]-5-[2-{2-[{N-(4-chlorobenzyl)-N-methyl}amino]ethoxy}phenyl]-thiophene-3-carboxamide a) The title compound was prepared from N-[2-(2-bromophenoxy)ethyl]-N-(4-chlorobenzyl)methylamine in a similar manner to Example 1 (a). After cooling, the solvent was evaporated and the residue was stirred with DCM and water. The DCM layer was chromatographed on silica in methanol-DCM mixtures, and relevant fractions were evaporated to a gum that was triturated with ether to afford the title compound as a solid.

MS (ES) 459 (M+H)$^+$.

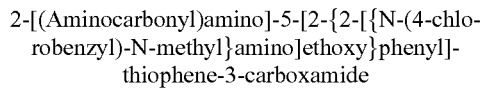

b) N-[2-(2-Bromophenoxy)ethyl]-N-(2-chlorobenzyl)methylamine

This was prepared from 2-(2-bromophenoxy)ethyl chloride and N-methyl-4-chlorobenzylamine in a similar manner to Example 1 (b) and purified by chromatography on silica gel eluting with DCM, affording the title compound as an oil.

$^1$H NMR (CDCl$_3$) 2.35 (s, 3H), 2.9 (t, 2H), 3.6 (s, 2H), 4.1 (t, 2H), 6.8-6.9 (m, 2H), 7.2-7.3 (m, 4H), 7.5 (d, 2H).

EXAMPLE 3

2-[(Aminocarbonyl)amino]-5-[2-{2-(benzylamino)ethoxy}phenyl]thiophene-3-carboxamide a) tert-Butyl N-[2-(2-{3-(aminocarbonyl)-2-[(aminocarbonyl)amino]thien-5-yl}phenoxy)ethyl]-N-benzylcarbamate (0.16 g) was dissolved in DCM (3 ml); thioanisole (0.5 g) and trifluoroacetic acid (1 ml) were added. The mixture was stirred for 30 min, then water (5 ml) was added and the mixture extracted with DCM. The DCM was added to a SCX cation exchange column and eluted with 30% methanol-DCM to remove the thioanisole, then with methanolic ammonia-DCM mixtures. The solvent was evaporated and the residue recrystallised from methanol affording the title compound as a white solid (0.04 g).

MS (ES) 411 (M+H)$^+$.

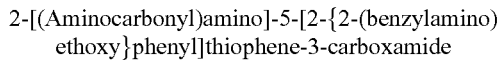

b) tert-Butyl N-[2-(2-{3-(aminocarbonyl)-2-[(aminocarbonyl)amino]thien-5-yl}phenoxy)ethyl]-N-benzylcarbamate This was prepared from tert-butyl N-benzyl-N-[2-(2-bromophenoxy)ethyl]carbamate in a similar manner to Example 1 (a), except that the DCM layer was chromatographed twice on silica in DCM-methanol mixtures affording the title compound as a resinous solid.

MS (ES) 511 (M+H)$^+$.

$^1$H NMR (DMSO-D6) 1.35 (s, 9H), 3.6 (t, 2H), 4.2 (t, 2H), 4.5 (s, 2H), 6.5 (s 2H), 6.9-7.4 (m, 10H), 7.5 (d, 1H), 7.6 (s, 1H), 10.9 (s, 1H)

c) tert-Butyl N-benzyl-N-[2-(2-bromo henoxy)ethyl]carbamate

A solution of di-t-butyl dicarbonate (0.96 g) in DCM (4 ml) was added over 5 min to a stirred solution of N-benzyl-N-[2-(2-bromophenoxy)ethyl]amine (1.3 g) in DCM (16 ml) and the mixture was stirred for 1.5 h, then concentrated to 6 ml, and diluted with isohexane (12 ml).

The solution was chromatographed on silica in isohexane-DCM mixtures affording the title compound as a colourless oil (0.9 g).

MS (ES) 350 (M+H-56)$^+$.

$^1$H NMR (DMSO-D6, 100° C.) 1.4 (s, 9H), 3.5 (t, 2H), 4.15 (t, 2H), 4.55 (s, 2H), 6.9 (t, 1H), 7.1 (d, 1H), 7.2-7.35 (m, 6H), 7.55 (d, 1H).

d) N-Benzyl-N-[2-(2-bromophenoxy)ethyl]amine

This was prepared from benzylamine and 1-bromo-2-(2-chloroethoxy)benzene by the method of Example 1 (b). The material obtained after chromatography on silica in DCM-methanolic ammonia mixtures was stirred in DCM and a solid removed by filtration. Evaporation of the mother liquors afforded the title compound as an oil.

$^1$H NMR (DMSO-D6) 2.9 (t, 2H), 3.2-3.3 (bs, 1H), 3.8 (s, 2H), 4.1 (t, 2H), 6.9 (t, 1H), 7.1 (d, 1H), 7.2-7.35 (m, 6H), 7.55 (d, 1H).

EXAMPLE 4

2-[(Aminocarbonyl)amino]-5-[2-{2-[N-benzyl-N-methylamino]ethoxy}phenyl]thiohene-3-carboxamide a) The title compound was prepared from N-benzyl-N-[2-(2-bromophenoxy)ethyl]methyl amine in a similar manner to Example 1 (a) except that after evaporation of the dimethoxyethane, the aqueous residue was extracted with DCM (100 ml). The latter was then extracted with 5% aqueous acetic acid, the acetic acid extracts adjusted to pH 8 with 10N potassium hydroxide solution and the resulting precipitate collected by filtration, washed with water and digested in methanol (5 ml), affording the title compound as a solid.

MS 425 (M+H)$^+$.

$^1$H NMR (DMSO-D6) 2.2 (s, 3H), 2.9 (t, 2H), 3.55 (s, 2H), 4.25 (t, 2H), 6.8 (s, 2H), 7.0 (t, 1H), 7.1 (d, 1H), 7.2-7.3 (m, 7H), 7.6 (d, 2H), 7.8 (s, 1H), 11.0 (s, 1H).

b) N-Benzyl-N-[2-(2-bromophenoxy)ethyl]methylamine

This was prepared from 1-bromo-2-(2-chloroethoxy)benzene and N-methyl benzylamine in a similar manner to Example (b) except that the mixture was stirred at 65° C. for 16 h.

MS (ES) 320 (M+H)$^+$.

$^1$H NMR (CDCl$_3$) 2.4 (s, 3H), 2.9 (t, 2H), 3.7 (s, 2H), 4.1 (t, 2H), 6.7-6.9 (m, 2H), 7.15-7.4 (m, 6H), 7.5 (d, 1H).

EXAMPLE 5

2-[(Aminocarbonyl)amino]-5-[2-{2-(1,3-dihydro-2H-isoindol-2-yl)ethoxy}phenyl]thiophene-3-carboxamide a) The title compound was prepared from 2-[2-(2-bromophenoxy)ethyl]isoindoline in a similar manner to Example 1 (a), except that the crude solid obtained was dissolved in DCM and this was extracted with 5% aqueous acetic acid; the acetic acid extracts were adjusted to pH 9 with sodium hydrogen carbonate solution and the resulting precipitate collected by filtration.

MS (ES) 423.2 (M+H)$^+$.

$^1$H NMR (DMSO-D6) 3.2 (t, 2H), 3.9 (s, 4H), 4.2 (t, 2H), 6.8 (bs, 2H), 7.0 (t, 1H), 7.1-7.3 (m, 7H), 7.5-7.7 (m, 2H), 7.75 (s, 1H).

b) 2-[2-(2-Bromophenoxy)ethyl]isoindoline

This was prepared in a similar manner to Example 1 (b) except that the mixture was stirred at 100° C. for 16 h and the product was purified by chromatography on silica in ethyl acetate-isohexane mixtures.

MS (ES) 318 (M+H)$^+$.

$^1$H NMR (CDCl$_3$) 3.2 (t, 2H), 4.1 (s, 4H), 4.2 (t, 2H), 6.8 (t, 1H), 6.9 (d, 1H), 7.2 (s, 4H), 7.3 (t, 1H), 7.5 (d, 1H).

EXAMPLE 6

2-[(Aminocarbonyl)amino]-5-[2-{[1-(4-fluorobenzyl)pyrrolidin-3-yl]oxy}phenyl]thiophene-3-carboxamide a) The title compound was prepared from 3-(2-bromophenoxy)-1-(4-fluorobenzyl)pyrrolidine in a similar manner to Example 1 (a) except that the concentrated reaction mixture was partitioned between DCM and saturated sodium carbonate. The solvent layer was washed (brine), dried and evaporated to leave an oil that was purified by cation exchange chromatography.

MS (ES) 455 (M+H)$^+$.

$^1$H NMR (DMSO-D6) 2.0 (m, 1H), 2.3 (m, 1H), 2.55 (m, 2H), 2.75 (m, 2H), 3.0 (m, 1H), 3.7 (m, 2H), 5.0 (m, 1H), 6.8 (br, 2H), 6.95 (m, 2H), 7.1 (m, 2H), 7.2 (br, 1H), 7.3 (m, 2H), 7.6 (m, 2H), 7.8 (s, 1H), 10.95 (s, 1H).

b) 3-(2-Bromophenoxy)-1-(4-fluorobenzyl)pyrrolidine

Sodium hydride (0.144 g, 60% dispersion in oil) was added portionwise to a stirred solution of 2-bromophenol (0.52 g) in dimethylacetamide (10 ml). After stirring for 15 min, a solution of 1-(4-fluorobenzyl)pyrrolidin-3-yl methanesulphonate (3.7 mmol) in dimethylacetamide (10 ml) was added portionwise and the resulting mixture was heated at 75° C. for 18 h.

The solvent was evaporated and the residue dissolved in ethyl acetate/water. The solvent phase was washed twice (brine), dried and evaporated to leave an oil that was purified by cation exchange chromatography giving the title compound (0.6 g).

MS (ES) 350 (M+H)$^+$.

$^1$H NMR (DMSO-D6) 1.6 (m, 1H), 2.05 (m, 1H), 2.3 (m, 1H), 2.7 (m, 2H), 3.1 (m, 1H), 3.6 (s, 2H), 4.8 (m, 1H), 6.8 (m, 2H), 7.0 (m, 2H), 7.2 (m, 3H), 7.55 (dd, 1H).

c) 1-(4-Fluorobenzyl)pyrrolidin-3-yl methanesulphonate

A solution of 1-(4-fluorobenzyl)pyrrolidin-3-ol (0.72 g) and triethylamine (0.62 ml) in toluene (50 ml) was cooled to 0° C. and methanesulphonyl chloride (0.34 ml) added dropwise with stirring. The mixture was allowed to warm to ambient temperature and stirred for a further 4 h. The reaction mixture was filtered and the filtrate evaporated to leave an oil which was used immediately.

d) 1-(4-Fluorobenzyl)pyrrolidin-3-ol

A solution of 3-pyrrolidinol (1.74 g) and 4-fluorobenzyl bromide (4.9 g) in acetone was stirred at ambient temperature for 24 h. After evaporation of the solvent, the residue was treated with 30% w/v potassium hydroxide solution and extracted twice with ethyl acetate. The combined solvent phase was washed with brine and dried. Evaporation of the solvent yielded an oil which was purified using cation exchange chromatography to give the title compound (0.72 g).

MS (ES) 196 (M+H)$^+$.

$^1$H NMR (CDCl$_3$) 1.75 (m, 1H), 2.2 (m, 2H), 2.3 (m, 2H), 2.5 (m, 1H), 2.6 (m, 1H), 2.8 (m, 1H), 3.6 (s, 2H), 4.35 (m, 1H), 7.0 (m, 1H), 7.25 (m, 2H).

EXAMPLE 7

2-[(Aminocarbonyl)amino]-5-[2-{[1-benzylpyrrolidin-3-yl]oxy}phenyl]thiophene-3-carboxamide a) The title compound was prepared from 1-benzyl-3-(2-bromophenoxy)pyrrolidine in a similar manner to Example 6 (a).

MS (ES) 437 (M+H)$^+$.

$^1$H NMR (DMSO-D6) 2.0 (m, 1H), 2.2 (m, 1H), 2.5 (m, 1H), 2.7 (m, 2H), 3.0 (m, 1H), 3.6 (m, 2H), 5.0 (m, 1H), 6.8 (br, 2H), 6.95 (m, 2H), 7.2 (m, 3H), 7.3 (m, 5H), 7.7 (s, 1H), 7.8 (m, 1H), 10.91 (s, 1H).

b) 1-Benzyl-3-(2-bromophenoxy)pyrrolidine

The title compound was prepared from 1-benzylpyrrolidin-3-yl methanesulphonate and 2-bromophenol in a similar manner to Example 6 (b) and purified using cation exchange chromatography.

MS (ES) 334 (M+H)$^+$.

$^1$H NMR (DMSO-D6) 2.0 (m, 1H), 2.3 (m, 1H), 2.7 (m, 3H), 3.15 (m, 1H), 3.7 (s, 2H), 4.8 (m, 1H), 6.8 (m, 2H), 7.25 (m, 6H), 7.5 (m, 1H).

c) 1-Benzyl-pyrrolidin-3-yl methanesulphonate

The title compound was prepared from 1-benzylpyrrolidin-3-ol in a similar manner to Example 6 (c).

MS (ES) 256 (M+H)$^+$.

EXAMPLE 8

2-[(Aminocarbonyl)amino]-5-[2-{2-[(4-fluorobenzyl)amino]ethoxy}phenyl]thiophene-3-carboxamide a) The title compound was prepared by treating tert-butyl N-[2-(2-{3-(aminocarbonyl)-2-[(aminocarbonyl)amino]thien-5-yl}phenoxy)ethyl]-N-[4-fluorobenzyl]carbamate with 10% aqueous trifluoroacetic acid for 2 h at ambient temperature followed by purification using cation exchange chromatography.

MS (ES) 429 (M+H)$^+$.

$^1$H NMR (DMSO-D6) 2.9 (m, 2H), 3.8 (s, 2H), 4.15 (m, 2H), 6.85 (br, 2H), 6.95 (m, 1H), 7.05 (m, 3H), 7.2 (m, 2H), 7.35 (m, 2H), 7.6 (m, 2H), 7.75 (s, 1H), 10.92 (s, 1H).

b) tert-Butyl N-[2-(2-{3-(aminocarbonyl)-2-[(aminocarbonyl)amino]thien-5-yl)phenoxy)ethyl]-N-[4-fluorobenzyl]carbamate The title compound was prepared from tert-butyl N-[2-(2-bromophenoxy)ethyl]-N-[4-fluorobenzyl]carbamate in a similar manner to Example 1 (a) except that the concentrated reaction mixture was partitioned between DCM and saturated sodium carbonate. The solvent layer was washed (brine), dried and evaporated to leave an oil. The pure product was obtained by silica chromatography eluting with DCM/methanol mixtures.

MS (ES) 529 (M+H)$^+$.

$^1$H NMR (DMSO-D6) 1.35 (s, 9H), 3.6 (m, 2H), 4.1 (m, 2H), 4.4 (m, 2H), 6.8 (m, 2H), 7.1 (m, 2H), 7.25 (m, 3H), 7.6 (m, 6H), 10.98 (s, 1H).

c) tert-Butyl N-[2-(2-bromophenoxy)ethyl]-N-[4-fluorobenzyl]carbamate

A solution of di-tert-butyl dicarbonate (1.86 g) in DCM (5 ml) was added over 5 min to a stirred solution of N-[2-(2-bromophenoxy)ethyl]-N-[4-fluorobenzyl]amine (2.5 g) in DCM (20 ml) and the resulting mixture was stirred at room temperature for 4 h. The reaction was diluted with DCM and then washed with water. After drying, the solvent was evaporated to yield an oil (2.9 g).

MS (ES) 424 (M+H)$^+$.

d) N-[2-(2-Bromophenoxy)ethyl]-N-[4-fluorobenzyl]amine

The title compound was prepared from 1-bromo-2-(2-chloroethoxy)benzene and 4-fluorobenzylamine in a similar manner to Example 1 (b).

MS (ES) 324 (M+H)$^+$.

EXAMPLE 9

2-[(Aminocarbonyl)amino]-5-[2-{2-(pyridin-3-ylmethylamino)ethoxy}phenyl]thiophene-3-carboxamide a) The title compound was prepared from tert-butyl N-[2-(2-{3-(aminocarbonyl)-2-[(aminocarbonyl)amino]thien-5- yl}phenoxy)ethyl]-N-[pyridin-3-ylmethyl]carbamate in a similar manner to Example 8 (a). Purification was achieved using cation exchange chromatography.

MS (ES) 412 (M+H)⁺.

¹H NMR (DMSO-D6) 3.3 (m, 2H), 4.2 (m, 2H), 4.3 (m, 2H), 6.9 (br, 2H), 7.1-7.3 (m, 5H), 7.7 (m, 2H), 7.8 (s, 1H), 7.9 (m, 1H), 8.5 (m, 1H), 8.6 (s, 1H), 10.95 (s, 1H).

b) tert-Butyl N-[2-(2-f 3-(aminocarbonyl)-2-[(aminocarbonyl)amino]thien-5-yl}phenoxy)ethyl]-N-[pyridin-3-ylmethyl]carbamate The title compound was prepared from tert-butyl N-[2-(2-bromophenoxy)ethyl]-N-[pyridin-3-ylmethyl]carbamate in a similar manner to Example 1 (a). Purification was achieved using cation exchange chromatography.

MS (ES) 512 (M+H)⁺.

c) tert-Butyl N-[2-(2-bromophenoxy)ethyl]-N-[pyridin-3-ylmethyl]carbamate

The title compound was prepared from N-[2-(2-bromophenoxy)ethyl]-N-[pyridin-3-ylmethyl]amine in a similar manner to Example 8 (c). Purification was achieved using cation exchange chromatography.

MS (ES) 407 (M+H)⁺.

¹H NMR (DMSO-D6) 1.5 (s, 9H), 3.6 (m, 2H), 4.2 (m, 2H), 4.8 (s, 2H), 6.8 (m, 2H), 7.2 (m, 2H), 7.55 (m, 1H), 7.6 (m, 1H), 8.5 (m, 1H), 8.6 (s, 1H).

d) N-[2-(2-Bromophenoxy)ethyl]-N-[pyridin-3-ylmethyl]amine

The title compound was prepared from 1-bromo-2-(2-chloroethoxy)benzene and (pyridin-3-ylmethyl)amine in a similar manner to Example 8 (d).

MS (ES) 307 (M+H)⁺.

¹H NMR (DMSO-D6) 3.1 (m, 2H), 4.05 (s, 2H), 4.2 (m, 2H), 6.8 (m, 2H), 7.2 (m, 3H), 7.55 (m, 1H), 7.6 (m, 1H), 8.55 (m, 1H).

EXAMPLE 10

2-[(Aminocarbonyl)amino]-5-[2-{2-(pyridin-2-ylmethylamino)ethoxy}phenyl]thiohene-3-carboxamide a) The title compound was prepared from tert-butyl N-[2-(2-{3-(aminocarbonyl)-2-[(aminocarbonyl)amino]thien-5-yl}phenoxy)ethyl]-N-[pyridin-2-ylmethyl]carbamate in a similar manner to Example 8 (a). Purification was achieved using cation exchange chromatography.

MS (ES) 412 (N+H)⁺.

¹H NMR (DMSO-D6) 3.4 (m, 2H), 4.4 (m, 4H), 6.9 (br, 2H), 7.1-7.3 (m, 6H), 7.7 (m, 2H), 7.8 (s, 1H), 7.9 (m, 1H), 8.5 (m, 1H), 8.6 (m, 1H), 10.95 (s, 1H).

b) tert-Butyl N-[2-(2-{3-(aminocarbonyl)-2-[(aminocarbonyl)amino]thien-5-yl}phenoxy)ethyl]-N-[pyridin-2-ylmethyl]carbamate The title compound was prepared from tert-butyl N-[2-(2-bromophenoxy)ethyl]-N-[pyridin-2-ylmethyl]carbamate in a similar manner to Example 1 (a). Purification was achieved using cation exchange chromatography.

MS (ES) 512 (M+H)⁺.

c) tert-Butyl N-[2-(2-bromophenoxy)ethyl]-N-[pyridin-2-ylmethyl]carbamate

The title compound was prepared from N-[2-(2-bromophenoxy)ethyl]-N-[pyridin-2-ylmethyl]amine in a similar manner to Example 8 (c). Purification was achieved using cation exchange chromatography.

MS (ES) 407 (M+H)⁺.

¹H NMR (DMSO-D6) 1.5 (s, 9H), 3.8 (m, 2H), 4.2 (m, 2H), 4.8 (s, 2H), 6.8 (m, 3H), 7.2 (m, 2H), 7.5 (m, 1H), 7.6 (m, 1H), 8.5 (m, 1H).

d) N-[2-(2-Bromophenoxy)ethyl]-N-[pyridin-2-ylmethyl]amine

The title compound was prepared from 1-bromo-2-(2-chloroethoxy)benzene and (pyridin-2-ylmethyl)amine in a similar manner to Example 8 (d).

MS (ES) 307 (M+H)⁺.

¹H NMR (DMSO-D6) 3.1 (m, 21), 4.05 (s, 2H), 4.2 (m, 2H), 6.8 (m, 2H), 7.2 (m, 31), 7.55 (m, 1H), 7.6 (m, 1H), 8.55 (m, 1H).

EXAMPLE 11

2-[(Aminocarbonyl)amino]-5-[2-{2-(pyridin-4-ylmethylamino)ethoxy}phenyl]thiophene-3-carboxamide a) The title compound was prepared from tert-butyl N-[2-(2-{3-(aminocarbonyl)-2-[(aminocarbonyl)amino]thien-5-yl}phenoxy)ethyl]-N-[pyridin-4-ylmethyl]carbamate in a similar manner to Example 8 (a). Purification was achieved using cation exchange chromatography.

MS (ES) 412 (M+H)⁺.

¹H NMR (DMSO-D6) 3.45 (m, 2H), 4.3 (m, 2H), 4.4 (m, 2H), 6.9 (br, 2H), 7.2 (m, 1H), 7.3 (m, 1H), 7.4 (m, 2H), 7.6 (m, 2H), 7.7 (m, 1H), 7.8 (s, 1H), 7.9 (m, 1H), 8.5 (m, 1H), 8.6 (m, 1H), 9.4 (m, 1H), 11.0 (s, 1H).

b) tert-Butyl N-[2-(2-{3-(aminocarbonyl)-2-[(aminocarbonyl)amino]thien-5-yl}phenoxy)ethyl]-N-[pyridin-4-ylmethyl]carbamate The title compound was prepared from tert-butyl N-[2-(2-bromophenoxy)ethyl]-N-[pyridin-4-ylmethyl]carbamate in a similar manner to Example 1 (a). Purification was achieved using cation exchange chromatography.

MS (ES) 512 (M+H)⁺.

c) tert-Butyl N-[2-(2-bromophenoxy)ethyl]-N-[pyridin-4-ylmethyl]carbamate

The title compound was prepared from N-[2-(2-bromophenoxy)ethyl]-N-[pyridin-4-ylmethyl]amine in a similar manner to Example 8 (c). Purification was achieved using cation exchange chromatography.

MS (ES) 407 (M+H)⁺.

¹H NMR (DMSO-D6) 1.5 (s, 9H), 3.6-3.8 (m, 2H), 4.2 (m, 2H), 4.8 (s, 2H), 6.8 (m, 3H), 7.2 (m, 2H), 7.6 (m, 2H), 8.55 (m, 1H).

d) N-[2-(2-bromophenoxy)ethyl]-N-[pyridin-4-ylmethyl]amine

The title compound was prepared from 1-bromo-2-(2-chloroethoxy)benzene and (pyridin-4-ylmethyl)amine in a similar manner to Example 8 (d).

MS (ES) 307 (M+H)+.

EXAMPLE 12

2-[(Aminocarbonyl)amino]-5-[2-[2-{N-(pyridin-3-ylmethyl)-N-methylamino]ethoxy}phenyl]thiophene-3-carboxamide a) The title compound was prepared from N-[2-(2-bromophenoxy)ethyl]-N-methyl-N-(pyridin-3-ylmethyl)amine in a similar manner to Example 1 (a) except that the concentrated reaction mixture was partitioned between DCM and saturated sodium carbonate. The solvent layer was washed (brine), dried and evaporated to an oil. The pure product was obtained by cation exchange chromatography.

MS (ES) 426 (M+H)+.

$^1$H NMR (DMSO-D6) 2.2 (s, 3H), 2.95 (m, 2H), 3.7 (s, 2H), 4.25 (m, 2H), 6.8 (br, 2H), 7.0 (m, 1H), 7.05 (m, 1H), 7.2 (m, 1H), 7.25 (m, 1H), 7.6 (m, 2H), 7.7 (m, 2H), 7.8 (s, 1H), 8.4 (m, 2H), 10.95 (s, 1H).

b) N-[2-(2-Bromophenoxy)ethyl]-N-methyl-N-(pyridin-3-ylmethyl)amine

The title compound was prepared from 1-bromo-2-(2-chloroethoxy)benzene and 3-(methylaminomethyl)pyridine in a similar manner to Example 1 (b).

MS (ES) 321 (M+H)+.

$^1$H NMR (DMSO-D6) 2.4 (s, 3H), 2.95 (m, 2H), 3.7 (s, 2H), 4.2 (m, 2H), 6.8 (m, 2H), 7.2 (m, 2H), 7.55 (m, 1H), 7.7 (m, 1H), 8.5 (m, 1H), 8.55 (m, 1H).

EXAMPLE 13

3-[(Aminocarbonyl)amino]-5-[2-{2-(1,3-dihydro-2H-isoindol-2-yl)ethoxy}phenyl]thiophene-2-carboxamide a) 2-Bromothiophene-4-carboxylic acid Prepared according to the method as described in J. Am. Chem. Soc., 1954, 76, 2445.

MS (ES) 205 (M-H)−

$^1$H NMR (DMSO-D6) 7.45 (s, 1H), 8.22 (s, 1H), 12.94 (bs, 1H).

b) 2-Bromo-4-(N-tert-butyloxycarbonyl)aminothiophene

2-Bromothiophene-4-carboxylic acid (3 g) was dissolved in dry warm t-butanol (24 ml). Triethylamine (2.02 ml) was added followed by diphenylphosphoryl azide (3.12 ml). The solution was heated slowly to reflux and heating continued at reflux overnight. The reaction mixture was then allowed to cool, poured into water (150 ml) and extracted with ethyl acetate (3×100 ml). The combined extracts were dried, filtered and evaporated. The crude product was purified by column chromatography, eluting with 5% ethyl acetate in hexane, to give a white solid (1.69 g).

MS (ES) 276 (M-H)—.

$^1$H NMR (DMSO-D6) 1.44 (s, 9H), 7.03 (s, 1H), 7.51 (s, 1H), 9.65 (s, 1H).

c) 5-Bromo-3-[(tert-butyloxycarbonyl)amino]thiophene-2-carboxylic acid

2-Bromo-4-(N-tert-butyloxycarbonyl)aminothiophene (1.68 g) was stirred in dry THF (45 ml) under argon and the solution was cooled to −78° C. Lithium diisopropylamide (7.55 ml, 2M solution) was added dropwise and stirring continued for 3.5 h. Powdered $CO_2$ (excess) was added and the mixture stirred for a further 10 min before allowing to warm to room temperature. Water (50 ml) was added, the THF was removed in vacuo and the aqueous phase was extracted with ethyl acetate (3×40 ml). The combined extracts were washed with 1M HCl solution (50 ml), water (50 ml) and brine (50 ml), dried, filtered and the solvent evaporated. The residue was triturated with DCM and the product collected by filtration as a pale yellow solid (1.57 g).

MS (ES) 320 (M-H)−

$^1$H NMR (DMSO-D6) 9.38 (s, 1H), 7.79 (s, 1H), 1.42 (s, 9H).

d) 5-Bromo-3-(tert-butyloxycarbonyl)aminothiophene-2-carboxamide

5-Bromo-3-[(tert-butyloxycarbonyl)amino]thiophene-2-carboxylic acid (0.80 g) was stirred in acetonitrile (80 ml). Hydroxybenztriazole (1.41 g) and 1-(3-dimethylaminopropyl)-3-ethylcarbodiimide hydrochloride (2.62 g) were added and stirring continued at room temperature for 10 min. Concentrated aqueous ammonia solution (8 ml) was added and the reaction mixture was heated to reflux for 1 h. The acetonitrile was removed by evaporation. Water (100 ml) was added and the mixture was sonicated and triturated. The resultant off-white solid was then collected by filtration, washed with water and dried under vacuum (0.763 g).

MS (ES) 319 (M-H)—.

$^1$H NMR (DMSO-D6) 1.45 (s, 9H), 7.63 (brs, 2H), 7.78 (s, 1H), 10.40 (s, 1H).

e) 3-Amino-5-bromothiophene-2-carboxamide

5-Bromo-3-(tert-butyloxycarbonyl)aminothiophene-2-carboxamide (0.76 g) was stirred in DCM (30 ml). Trifluoroacetic acid (5 ml) was added, the solution was stirred at room temperature for 1 h, poured into saturated aqueous sodium hydrogen carbonate solution (200 ml) and extracted with DCM (3×100 ml). The combined extracts were washed with brine (150 ml), dried, filtered and evaporated to give a yellow solid (0.511 g).

MS (ES) 221 (M+H)+.

$^1$H NMR (DMSO-D6) 6.50 (bs, 2H), 6.69 (s, 1H), 6.87 (bs, 2H).

f) 3-[(Aminocarbonyl)amino-5-bromothiophene-2-carboxamide

3-Amino-5-bromothiophene-2-carboxamide (0.25 g) was stirred in anhydrous THF (10 ml), cooled to 0° C. and trichloroacetylisocyanate (0.148 ml) added dropwise. The mixture was allowed to warm to ambient temperature, stirred for 1.5 h and 2M ammonia in methanol (16 ml) added. After 1.5 h, the solvents were evaporated and the residue triturated with diethyl ether and dried in vacuo to give the title compound as a yellow solid (0.26 g).

MS (ES) 264 (M+H)$^+$.

$^1$H NMR (DMSO-D6) 6.63 (bs, 2H), 7.41 (bs, 2H), 7.97 (s, 1H), 10.02 (s, 1H).

g) 3-[(Aminocarbonyl amino]-5-[2-{2-(1,3-dihydro-2H-isoindol-2-yl)ethoxy}phenyl]thiophene-2-carboxamide The title compound was prepared from 2-[2-(2-bromophenoxy)ethyl]isoindoline and 3-[(aminocarbonyl)amino]-5-bromothiophene-2-carboxamide in a similar manner to Example 1 (a). The pure product was obtained by silica chromatography eluting with DCM/methanol mixtures.

MS (ES) 423 (M+H)$^+$.

$^1$H NMR (DMSO-D6) 3.2 (m, 2H), 3.95 (s, 4H), 4.3 (m, 2H), 6.5 (br, 2H), 7.0 (s, 1H), 7.2 (m, 5H), 7.3 (m, 2H), 7.6 (m, 2H), 8.4 (s, 1H), 10.0 (s, 1H).

Pharmacological and Pharmacokinetic Evaluation of Compounds

IKK-2 Filter Kinase Assay

Compounds were tested for inhibition of IKK-2 using a filter kinase assay. The test compounds were dissolved to 10 mM in dimethylsulphoxide (DMSO). The compounds were then diluted 1 in 40 in kinase buffer (50 mM Tris, pH 7.4 containing 0.1 mM EGTA, 0.1 mM sodium orthovanadate and 0.1% β-mercaptoethanol). 1 in 3 serial dilutions were made from this solution with 2.5% DMSO in kinase buffer. 20 µl of compound dilution was added to wells of a 96 well plate in duplicate. 20 µl 2.5% DMSO in kinase buffer instead of compound was added to control wells (0% inhibition). 20 µl 0.5 M EDTA was added instead of compound to background wells (100% inhibition).

10 µl of a mixture of magnesium acetate, unlabelled ATP, and $^{33}$P-labelled ATP was added to each well made such that the final concentration was 10 mM magnesium acetate, 1 µM ATP and 0.1 µCi $^{33}$P ATP. 20 µl of a mixture of IKK-2 (0.15 µg/well), 1-53 GST-IκB (0.5 µg/well) and bovine serum albumin (BSA) (8.5 µg/well) was added to each well to start the reaction. The final reaction volume was 50 µl.

The kinase reactions were incubated at 21° C. for 80 minutes and the reaction stopped by precipitating the protein by the addition of an equal volume (50 µl) of 20% trichloroacetic acid (TCA). The precipitate was allowed to form for 10 minutes and then filtered onto a GF/C unifilter 96 well plate. Each filter was washed twice with approximately 1 ml 2% TCA. The filter plate was dried at 30-40° C. for 60 minutes, 20 µl scintillant was added to each well and the plate sealed and radioactivity counted on a Packard Topcount microplate scintillation counter.

When tested in the above assay, the compounds of Examples 1 to 13 gave IC$_{50}$ values of less than 10 µM indicating that they are expected to show useful therapeutic activity.

IKK-1 Filter Kinase Assay

The selectivity of compounds was assessed by testing them for inhibition of IKK-1 sing a filter kinase assay. The assay conditions were identical to the IKK-2 filter kinase assay except that a mixture of IKK-1 (0.25 µg/well) and 1-53 GST IκB (9 µg/well) was added to each well to start the reaction.

Inhibition of LPS-induced TNFα production by PBMCs

The effect of test compounds on nuclear factor kappa B (NFκB) activation in cells was assessed by measuring inhibition of tumour necrosis factor alpha (TNFα) production by human peripheral blood mononuclear cells (PBMCs) stimulated by bacterial lipopolysaccharide (LPS).

Human blood (250 ml), anticoagulated with heparin, was collected from healthy volunteers. Aliquots of blood (25 ml) were layered on 20 ml Lymphoprep (Nycomed) in 50 ml polypropylene centrifuge tubes. The tubes were centrifuged (Sorval RT600B) at 2,500 rpm for 30 minutes. The cloudy layer containing PBMCs was collected with a fine tipped Pasteur pipette, transferred into 8 clean polypropylene centrifuge tubes (approximately 10 ml per tube) and diluted to 50 ml with phosphate-buffered saline (PBS). These tubes were centrifuged at 2,000 rpm for 8 minutes. PBS (10 ml) was added to each cell pellet and the cells were gently re-suspended. The cells were pooled in 4 centrifuge tubes, PBS was added to each tube to make the volume up to 50 ml and the tubes were centrifuged at 1,400 rpm for 8 minutes. The cell pellets were again re-suspended in 10 ml PBS, pooled in 2 centrifuge tubes, the volume made up to 50 ml with PBS and the tubes centrifuged at 900 rpm for 10 minutes.

The final cell pellets were gently re-suspended in 10 ml tissue culture medium (RPMI containing 1% heat-inactivated human serum, L-glutamine and penicillin and streptomycin), combined into 1 tube and the volume made up to 30 ml with RPMI medium. The cells were counted and the cell suspension was diluted to 2.6×10$^6$ cells/ml.

Test compounds were dissolved in DMSO to 10 mM and diluted 1 in 250 (40 µM) with RPMI medium. The compounds were then serially diluted 1 in 3 with 0.4% DMSO in RPMI medium. Aliquots of test compound dilutions (50 µl) were transferred to the wells of a 96-well plate. Control wells contained 0.4% DMSO in RPMI instead of compound.

Aliquots of the cell suspension (100 µl) were added to each well and the plates incubated at 37° C. for 30 minutes. 50 VI of 40 µg/ml LPS (Sigma, L-4130) was added to wells to stimulate TNFα production by the cells and the plates were incubated overnight at 37° C. RPMI medium (50 VI) was added to negative control wells instead of LPS. The final incubation volume was 200 µl.

Plates were centrifuged for 4 minutes at 1,200 rpm and supernatants were removed for measurement of TNFα concentration. Viability of the remaining cell pellet was measured using WST-1 reagent (Boehringer Mannheim, 1044807). 100 µl RPMI medium containing 10 µl WST-1 reagent was added to each well and the plates were incubated for 0.5 to 3 h. The absorbance at 450 nm was then measured using a 96-well plate spectrophotometer.

TNFα in the supernatants (freshly harvested or stored frozen at −20° C.) were measured using an enzyme-linked immunosorbant assay (ELISA). The ELISA plate was prepared by coating the wells of a 96 well plate with a sheep anti-human TNFα monoclonal antibody (100 µl of 1 µg/ml antibody diluted in coating buffer; 0.5 M carbonate/bicarbonate buffer, pH 9.6 containing 0.2 g/l sodium azide) and incubating overnight at 4° C. Blank wells were not coated. The wells were washed once with 0.1% BSA in PBS containing 0.05% Tween (PBS/Tween) then incubated for 1 h at room temperature with 1% BSA in coating buffer (200 µl). The wells were then washed 3 times with 0.1% BSA in PBS/Tween.

The samples of supernatant from the PBMC incubation were diluted 1 in 3 with 1% BSA in PBS/Tween. 100 pl aliquots of these dilutions were added to the ELISA plate. Other wells contained 100 µl TNFα standard (10, 3.3, 1.1, 0.37, 0.12, 0.04, 0.014 and 0 ng/ml). The ELISA plate was incubated at room temperature for 2 h before the wells were washed 3 times with 0.1% BSA in PBS/Tween. A rabbit anti-human TNFα antibody (100 µl of a 2.5 µg/ml solution) was added to each well and the plate incubated at room temperature for 1.5 h. The wells were then washed 3 times with 0.1% BSA in PBS/Tween. Goat anti-rabbit IgG-horse radish peroxidase conjugate (ICN, 674371; 100 µl of a 1 in 10,000 dilution) was added to each well and the plate incubated at room temperature for 1.5 h. The wells were washed 3 times with 0.1% BSA in PBS/Tween.

Peroxidase substrate was prepared by dissolving a 1 mg TMB tablet (Sigma, T-5525) in 100 µl DMSO (100 µl) and adding this and 36 µl UHPO (BDH, 30559; 1 g tablet dissolved in 25 ml distilled water) to 10 ml 0.1M citrate/acetate buffer, pH6. 100 µl substrate was added to each well and the plate incubated in the dark at room temperature for approximately 30 minutes. The reaction was stopped by adding 25 Pl 2 M sulphuric acid to each well. The absorbance at 450 nm was measured in a 96 well plater spectrophotometer.

Assessment of Compound Permeability and Efflux Potential using CACO-2 Cell Monolayers.

Caco-2 cells are a cell line derived from human colon cancer cells. The Caco-2 cells retain many of the properties of the human gut, including tight junctions and transporter proteins (e.g. pgp transporter), and are used primarily to assess the potential of compounds to be absorbed after oral administration. In this assay protocol, transports in the apical to basolateral direction (A-B direction) as well as in the opposite direction (B-A direction) are determined to assess both permeability and efflux potentials of the test compounds.

Cells are seeded at a density of 100,000 cells/well onto 1 µm filters within each well of 24-well plates (Beckton-Dickinson, UK) and grown until an intact monolayer of the cells is formed across each well (14 days).

When ready for use the intactness of the monolayers is assessed using measurement of the Trans-Epithelial Resistance (TEER) within each well. If TEERs are acceptable, each test compound is added to pH 7.4 buffer to a concentration of 10 µM in either the upper (Apical; A) or lower (Basolateral; B) chambers of the individual wells of the 24-well plates in duplicate, resulting in replicate measurements of the permeability of each compound through the monolayers in both the A-B and B-A directions. Four reference compounds are incubated alongside test compounds for quality control purposes (low, medium and high permeability plus one known efflux substrate).

After mixing, an aliquot of the donor chamber is taken immediately for analysis (TO). The plates are then incubated for 120 min at 37° C., after which a further aliquot is taken from the donor chamber (used to assess recovery over the duration of the experiment), while a similar aliquot is taken from the recipient chamber at this time (T120 sample).

All sample manipulations are undertaken on a Tecan Genesis RS200 robot.

All samples are analysed using LC-electrospray MS (both + and − mode), and peak areas used to quantify each test agent.

From the data obtained the rate of transfer (Papp) of each compound across the monolayer is calculated in either the A-B or B-A directions. From the Papp(A-B) data, the potential human absorption is categorised as LOW (Papp<=0.5× $10^6.cm^2.sec^{-1}$), PARTIAL (Papp>0.5<=$2.9 \times 10^6$ $cm^2.sec^{-1}$) or HIGH (Papp>$2.9 \times 10^6.cm^2.sec^{-1}$), while from the Papp(B-A)/Papp(A-B) ratio, the potential for efflux of the test compound is assessed, where a ratio≧5 is categorised as HIGH, and <5 is categorised as LOW.

Results

| Compound | Caco-2 Assay | | |
| --- | --- | --- | --- |
| | Inhibition of IKK-2 (µM) | Papp ($cm^2 \cdot sec^{-1}$ × $10^{-6}$) | Papp (B-A)/Papp(A-B) Ratio |
| Example 4 | 0.04 | 13.4 | 0.83 |
| Example 5 | 0.15 | 14.3 | 0.66 |
| Example 7 | 0.04 | 15.7 | 1.07 |
| Example 13 | 1.43 | 23.6 | 1.26 |
| Example 82, WO 01/58890 | 0.26 | 0.1 to 0.4 | 64 to 472 |
| 2-[(Aminocarbonyl)amino]-5-(2-[{1-methylpyrrolidin-3-yl}oxy]phenyl)-3-thiophenecarboxamide | 0.01 | 2.19 | 8.14 |
| 2-[(Aminocarbonyl)amino]-5-(2-{[1-(2-methoxyethyl)-pyrrolidin-3-yl]oxy}phenyl)-3-thiophenecarboxamide | 0.03 | 1.86 | 5.88 |

The invention claimed is:

1. A compound of formula (I)

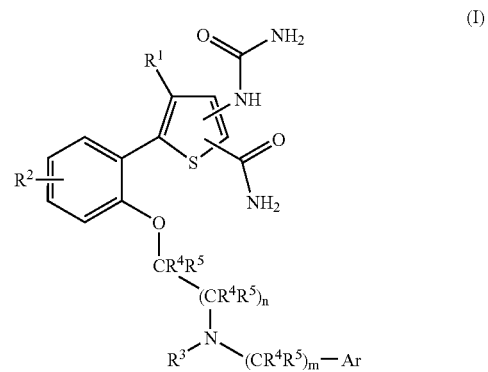

in which:

$R^1$ represents H or $CH_3$;

$R^2$ represents H, halogen, cyano, C1 to 2 alkyl, trifluoromethyl or C1 to 2 alkoxy;

n represents an integer 1, 2 or 3;

m represents an integer 0, 1, 2 or 3;

$R^3$ represents H, C2 to 4 alkenyl or C1 to 4 alkyl; said alkyl group being optionally further substituted by CN, C1 to 4 alkoxy, C1 to 4 alkyl-$SO_2$-or one or more fluoro atoms;

$R^4$ and $R^5$ independently represent H or C1 to 2 alkyl; and each $R^4$, each $R^5$ and each group $CR^4R^5$ is selected independently;

Ar represents a phenyl; said phenyl ring being optionally substituted by one or more substituents selected independently from halogen, cyano, C1 to 2 alkyl, trifluoromethyl, C1 to 2 alkoxy, $NR^6R^7$, —$CONR^6R^7$, —$COOR^6$, —$NR^6COR^7$, —$S(O)_pR^6$, —$SO_2NR^6R^7$ and —$NR^6SO_2R^7$;

$R^6$ and $R^7$ independently represent H, C2 to 4 alkenyl or C1 to 4 alkyl; said alkyl or alkenyl groups being optionally further substituted by one or more halogen atoms;

p represents an integer 0, 1 or 2;

and pharmaceutically acceptable salts thereof.

2. A compound of formula (I), according to claim 1, wherein n represents the integer 1.

3. A compound of formula (I), according to claim 1, wherein $R^1$ represents H.

4. A compound of formula (I), according to claim 1, in which each $R^4$ and each $R^5$ represents H.

5. A compound of formula (I), according to claim 1, in which m represents the integer 1.

6. A process for the preparation of a compound of formula (I), according to claim 1, which comprises:

(a) reaction of a compound of formula (II):

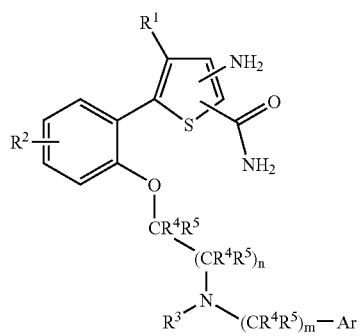

(II)

wherein $R^1$, $R^2$, $R^3$, $R^4$, $R^5$, Ar, m and n are as defined in claim 1, with an isocyanate; or (b) reaction of a compound of formula (III)

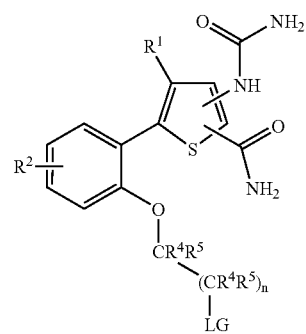

(III)

wherein $R^1$, $R^2$, $R^4$, $R^5$ and n are as defined in claim 1 and LG represents a leaving group, with an amine ($R^3NH(CR^4R^5)_m$-Ar) wherein $R^3$, $R^4$, $R^5$, Ar and m are as defined in claim (c) reaction of a compound of formula (IV)

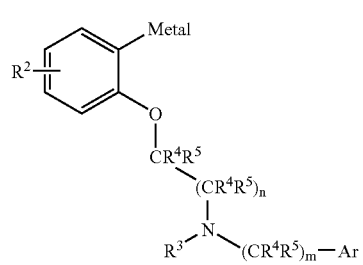

(IV)

wherein $R^2$, $R^3$, $R^4$, $R^5$, m, n and Ar are as defined in claim 1, with a compound of formula (V)

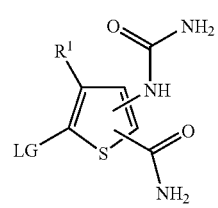

(V)

wherein $R^1$ is as defined in claim 1 and LG represents a leaving group; or (d) reaction of a compound of formula (VI)

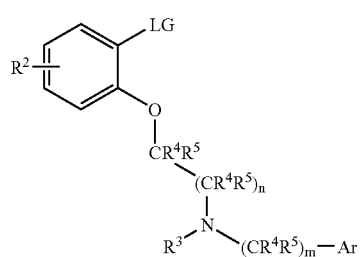

(VI)

wherein $R^2$, $R^3$, $R^4$, $R^5$, m, n and Ar are as defined in claim 1 and LG represents a leaving group, with a compound of formula (VII)

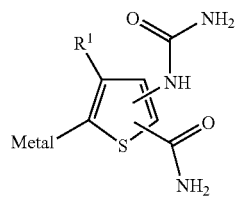

(VII)

wherein $R^1$ as defined in claim 1;

and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

7. A pharmaceutical composition comprising a compound of formula (I), or a pharmaceutically acceptable salt thereof, as claimed in claim 1 in association with a pharmaceutically acceptable adjuvant, diluent or carrier.

8. A pharmaceutical composition adapted for administration by inhalation or insufflation comprising a compound of formula (I), or a pharmaceutically acceptable salt thereof, as claimed in claim 1 in association with a pharmaceutically acceptable adjuvant, diluent or carrier.

9. A process for the preparation of a pharmaceutical composition which comprises mixing a compound of formula (I), or a pharmaceutically acceptable salt thereof, as claimed in claim 1 with a pharmaceutically acceptable adjuvant, diluent or carrier.

10. A method for the treatment of inflammatory disease selected from the group consisting of asthma, rheumatoid arthritis, multiple sclerosis, and chronic obstructive pulmonary disease; the method comprising administering to a person suffering from said inflammatory disease a therapeutically effective amount of a compound of formula (I), or a pharmaceutically acceptable salt thereof, as claimed in claim 1.

11. The method as claimed in claim 10 wherein the disease is rheumatoid arthritis.

12. The method as claimed in claim 10 wherein the disease is chronic obstructive pulmonary disease.

\* \* \* \* \*

UNITED STATES PATENT AND TRADEMARK OFFICE
CERTIFICATE OF CORRECTION

PATENT NO. : 7,553,868 B2
APPLICATION NO. : 10/542044
DATED : June 30, 2009
INVENTOR(S) : Andrew David Morley and Jeffrey Philip Poyser It is certified that error appears in the above-identified patent and that said Letters Patent is hereby corrected as shown below:

Title Page, Item (56), (U.S. Patent Documents), line 1, "7,166,369" should read --7,166,639--.

Column 27, line 53, "$R^3, R^4, R^5,$" should read -- $R^3, R^4, R^5$, --.

Column 27, line 54, "claim" should read -- claim 1 --.

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,553,868 B2 | Page 1 of 1 |
| APPLICATION NO. | : 10/542044 | |
| DATED | : June 30, 2009 | |
| INVENTOR(S) | : Morley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 173 days.

Signed and Sealed this

Twenty-fifth Day of January, 2011

David J. Kappos
*Director of the United States Patent and Trademark Office*